US011058473B2

(12) United States Patent
Zhang et al.

(10) Patent No.: US 11,058,473 B2
(45) Date of Patent: Jul. 13, 2021

(54) RECOGNITION, MONITORING, AND IMAGING METHOD AND SYSTEM FOR THERMAL ABLATION REGION BASED ON ULTRASONIC DEEP LEARNING

(71) Applicant: Xi'an Jiaotong University, Xi'an (CN)

(72) Inventors: Siyuan Zhang, Xi'an (CN); Shan Wu, Xi'an (CN); Shaoqiang Shang, Xi'an (CN); Zhiwei Cui, Xi'an (CN); Tianqi Xu, Xi'an (CN); Mingxi Wan, Xi'an (CN)

(73) Assignee: Xi'an Jiaotong University, Xi'an (CN)

( * ) Notice: Subject to any disclaimer, the term of this patent is extended or adjusted under 35 U.S.C. 154(b) by 290 days.

(21) Appl. No.: 16/278,371

(22) Filed: Feb. 18, 2019

(65) Prior Publication Data

US 2020/0121376 A1    Apr. 23, 2020

(30) Foreign Application Priority Data

Oct. 22, 2018   (CN) .......................... 201811226651.7

(51) Int. Cl.
*A61B 18/04* (2006.01)
*A61B 90/00* (2016.01)
(Continued)

(52) U.S. Cl.
CPC .......... *A61B 18/04* (2013.01); *A61B 18/1815* (2013.01); *A61B 90/37* (2016.02);
(Continued)

(58) Field of Classification Search
CPC ................ A61B 18/04; A61B 18/1815; A61B 2017/00084; A61B 2018/00333;
(Continued)

(56) References Cited

U.S. PATENT DOCUMENTS 6,095,150 A * 8/2000 Panescu ................. A61B 90/36
128/899
9,615,878 B2 * 4/2017 Nair ..................... A61B 18/1492
(Continued)

FOREIGN PATENT DOCUMENTS

CN        1168625 A    12/1997
CN        1847824 A    10/2006
(Continued)

OTHER PUBLICATIONS

Chinese Patent Office, Notice of Grant issued in CN Application No. 201811226651.7 dated Apr. 23, 2020 and English Translation (3 pages).
(Continued)

*Primary Examiner* — Michael F Peffley
(74) *Attorney, Agent, or Firm* — Wood Herron & Evans LLP (57) ABSTRACT

A recognition, monitoring, and imaging method and system are provided for a thermal ablation region based on ultrasonic deep learning. The recognition method includes obtaining original ultrasonic radiofrequency data, an ultrasonic image, and an optical image during thermal ablation; making ultrasonic radiofrequency data points and pixels in the optical image correspond in a one-to-one manner, and determining a spatial position correspondence between the ultrasonic radiofrequency data points and the optical image; determining a thermal ablation region image according to the spatial position correspondence; constructing a deep learning model according to the thermal ablation region image; superposing a thermal ablation classification image to the ultrasonic image, to determine a to-be-recognized thermal ablation image; and recognizing a thermal ablation region in the ultrasonic image according to the to-be-recognized thermal ablation image. The method and system
(Continued)

improve recognition accuracy of the thermal ablation region in the ultrasonic image.

4 Claims, 5 Drawing Sheets

(51) Int. Cl.
  *A61B 18/18* (2006.01)
  *A61B 17/00* (2006.01)
  *A61B 18/00* (2006.01)
  *A61N 7/02* (2006.01)
(52) U.S. Cl.
  CPC ............ *A61B 2017/00084* (2013.01); *A61B 2018/00333* (2013.01); *A61B 2018/00547* (2013.01); *A61B 2018/00577* (2013.01); *A61B 2018/00642* (2013.01); *A61B 2018/00702* (2013.01); *A61B 2018/00791* (2013.01); *A61B 2090/378* (2016.02); *A61N 7/02* (2013.01)
(58) Field of Classification Search
  CPC A61B 2018/00547; A61B 2018/00577; A61B 2018/00642; A61B 2018/00702; A61B 2018/00791; A61B 2034/105; A61B 2034/107; A61B 2034/2055; A61B 2034/2063; A61B 2034/2065; A61B 2090/364; A61B 2090/373; A61B 2090/378; A61B 90/37; A61N 7/02; G06N 3/0454; G06N 3/08
  See application file for complete search history.

(56) References Cited

U.S. PATENT DOCUMENTS 9,649,127 B2 * 5/2017 Burdette ............... A61B 8/485
2002/0188196 A1 12/2002 Burbank et al.

FOREIGN PATENT DOCUMENTS

| | | |
|---|---|---|
| CN | 101623203 A | 1/2010 |
| CN | 103948402 A | 7/2014 |
| CN | 104013433 A | 9/2014 |
| CN | 104398271 A | 3/2015 |
| CN | 106037815 A | 10/2016 |

OTHER PUBLICATIONS

Chinese Patent Office, Office Action issued in CN Application No. 201811226651.7 dated Jan. 3, 2020 and English Translation (11 pages).

* cited by examiner

RECOGNITION, MONITORING, AND IMAGING METHOD AND SYSTEM FOR THERMAL ABLATION REGION BASED ON ULTRASONIC DEEP LEARNING

CROSS-REFERENCE TO RELATED APPLICATION

This application claims priority to Chinese application number 201811226651.7, filed on Oct. 22, 2018. The above-mentioned patent application is incorporated herein by reference in its entirety.

TECHNICAL FIELD

The present invention relates to the field of ultrasonic monitoring imaging, and more particularly, relates to a recognition, monitoring, and imaging method and system for a thermal ablation region.

BACKGROUND

Tumor thermal ablation is an in-situ treatment technology in which a method is used to heat a tumor tissue to exceed its heat-resistant temperature to produce coagulative necrosis to kill cancer cells. With the development of modern medical imaging technologies, a minimally invasive or non-invasive thermal ablation technology has been widely applied in clinical treatment. At present, main clinical application methods of the thermal ablation treatment technology include high-intensity focused ultrasound, radiofrequency ablation, laser ablation, and microwave ablation. High-intensity focused ultrasound has many advantages such as a non-invasive effect, high efficiency, and good focusing performance, has been widely applied in clinical practice, and is mainly applied in the treatment of breast cancer, prostate cancer, and other diseases. In a laser treatment process, a laser knife is not in direct contact with a tissue, and therefore laser treatment can greatly reduce complications, and plays a vital role in the treatment of gynecological diseases such as cervical erosion, Naboth cyst, cervical ectropion, and cervical polyp. Like radiofrequency ablation, microwave ablation does not depend on an electrical conductivity of a tissue and can form high temperature inside a tumor within a short time, to produce heat coagulation to kill tumor cells. With the development of treatment technologies, medical imaging technologies, and microwave electrode manufacturing technologies, a microwave ablation treatment technology is increasingly applied in treatment of tumors in visceral organs such as liver, kidney, lung, and thyroid.

While ensuring the effectiveness of thermal ablation treatment, complications should also be prevented. Therefore, during ablation of a tumor tissue, it is necessary to avoid damage to surrounding normal tissues or organs as much as possible. The safe and effective application of thermal ablation in clinical treatment depends on a monitoring imaging technology in a treatment process. A modern medical imaging technology plays a crucial role in the scientific preoperative planning of microwave ablation treatment, real-time monitoring in the treatment process, and post-treatment therapeutic effect evaluation. At present, a conventional ultrasonic imaging method is usually used for monitoring imaging of microwave and radiofrequency ablation treatment. An ultrasonic image mainly reflects the echo signal strength of a tissue. Many bubbles are produced in a thermal ablation region at high temperature, leading to ultrasonic echo enhancement in the area. Strong echo is presented in the ablation region, but the strong echo disappears when the bubbles are dissipated. In addition, in the thermal ablation process, not all thermal ablation regions produce bubbles. Under normal circumstances, an area in which bubbles are located is smaller than an actual thermal damage area. Therefore, clinicians cannot accurately obtain a microwave ablation region by using ultrasound. In addition, after thermal ablation ends, bubbles in the thermal damage area are dissipated. Due to a low contrast between the ablation region and a normal tissue area in the ultrasonic image, it is difficult to detect the thermal damage in the conventional ultrasonic image. Therefore, it is relatively difficult to achieve an ideal effect by using a conventional ultrasonic image for monitoring imaging of thermal ablation.

Therefore, it would be desirable to provide a recognition, monitoring, and imaging method and system for a thermal ablation region based on ultrasonic deep learning, to resolve a problem of low recognition accuracy of a thermal ablation region in an ultrasonic image.

SUMMARY

To achieve the above objective, the present invention provides the following solution, in one embodiment: A recognition, monitoring, and imaging method for a thermal ablation region based on ultrasonic deep learning includes: obtaining original ultrasonic radiofrequency data, an ultrasonic image, and an optical image during thermal ablation, where the original ultrasonic radiofrequency data includes a plurality of ultrasonic radiofrequency data points; the ultrasonic radiofrequency data point is an ultrasonic scattering echo signal collected by an ultrasonic imaging device; the plurality of ultrasonic radiofrequency data points form an ultrasonic radiofrequency data matrix; and the optical image is captured by a mobile phone or a camera; making the ultrasonic radiofrequency data points and pixels in the optical image correspond in a one-to-one manner, and determining a spatial position correspondence between the ultrasonic radiofrequency data points and the optical image; determining a thermal ablation region image according to the spatial position correspondence; constructing a deep learning model according to the thermal ablation region image, where the deep learning model includes a convolutional neural network, a cyclic neural network, and a deep neural network; determining a thermal ablation classification image according to the deep learning model; superposing the thermal ablation classification image to the ultrasonic image, to determine a to-be-recognized thermal ablation image; and recognizing a thermal ablation region in the ultrasonic image according to the to-be-recognized thermal ablation image.

In one aspect, the determining a thermal ablation region image according to the spatial position correspondence specifically includes: cropping the optical image to determine a cropped optical image; obtaining an ablation applicator position in the cropped optical image and an ablation applicator position in the ultrasonic image; making the ablation applicator position in the cropped optical image and the ablation applicator position in the ultrasonic image overlap with each other, to determine an overlapping ablation applicator position; and performing interpolation processing on the cropped optical image by using the overlapping ablation applicator position as a center, to determine the thermal ablation region image.

In another aspect, after the performing interpolation processing on the cropped optical image by using the overlapping ablation applicator position as a center, to determine the thermal ablation region image, the method further includes: performing binarization processing on the thermal ablation region image to determine a binary image, where a classification label corresponding to a thermal ablation region in the binary image is 1, and a classification label corresponding to a peripheral area of the thermal ablation region is 0, and the binary image includes a plurality of ultrasonic radiofrequency data points and a classification label corresponding to the ultrasonic radiofrequency data point; traversing the ultrasonic radiofrequency data matrix to divide the ultrasonic radiofrequency data points into a training sample and a test sample; and determining, according to the binary image, a training classification label corresponding to the training sample and a test classification label corresponding to the test sample.

In a further aspect, the constructing a deep learning model according to the thermal ablation region image, where the deep learning model includes a convolutional neural network, a cyclic neural network, and a deep neural network specifically includes: obtaining an ultrasonic radiofrequency data matrix corresponding to the binary image and the classification label corresponding to the ultrasonic radiofrequency data point; determining an ultrasonic scattering echo spectrum estimation parameter and an ultrasonic statistical parameter from scattering echo according to the ultrasonic radiofrequency data matrix, where the ultrasonic scattering echo spectrum estimation parameter includes an ultrasonic attenuation parameter, an ultrasonic backscattering parameter, and an ultrasonic scattering sub-characteristic parameter, and the ultrasonic statistical parameter from scattering echo includes an ultrasonic Nakagami parameter, an ultrasonic entropy parameter, and an ultrasonic scattering density parameter; obtaining a convolutional neural network parameter, where the convolutional neural network parameter includes a convolution kernel size, a number of hidden layers, and a number of feature maps of each layer; and constructing the deep learning model according to the convolutional neural network parameter by sequentially inputting the training sample, the ultrasonic scattering echo spectrum estimation parameter, the ultrasonic statistical parameter from scattering echo, and the classification label corresponding to the ultrasonic radiofrequency data point, where the deep learning model includes the convolutional neural network, the cyclic neural network, and the deep neural network.

In another embodiment according to the present invention, a recognition, monitoring, and imaging system for a thermal ablation region based on ultrasonic deep learning includes: a module for obtaining original ultrasonic radiofrequency data and optical image, configured to obtain original ultrasonic radiofrequency data, an ultrasonic image, and an optical image during thermal ablation, where the original ultrasonic radiofrequency data includes a plurality of ultrasonic radiofrequency data points; the ultrasonic radiofrequency data point is an ultrasonic scattering echo signal collected by an ultrasonic imaging device; the plurality of ultrasonic radiofrequency data points form an ultrasonic radiofrequency data matrix; and the optical image is captured by a mobile phone or a camera; a module for determining spatial position correspondence, configured to make the ultrasonic radiofrequency data points and pixels in the optical image correspond in a one-to-one manner, and determine a spatial position correspondence between the ultrasonic radiofrequency data points and the optical image; a module for determining a thermal ablation region image, configured to determine a thermal ablation region image according to the spatial position correspondence; a module for constructing a convolutional neural network, configured to construct a deep learning model according to the thermal ablation region image, where the deep learning model includes a convolutional neural network, a cyclic neural network, and a deep neural network; a module for determining a thermal ablation classification image, configured to determine a thermal ablation classification image according to the deep learning model; a module for determining a to-be-recognized thermal ablation image, configured to superpose the thermal ablation classification image to the ultrasonic image, to determine a to-be-recognized thermal ablation image; and a recognition module, configured to recognize a thermal ablation region in the ultrasonic image according to the to-be-recognized thermal ablation image.

In one aspect, the module for determining a thermal ablation region image specifically includes: a cropping unit, configured to crop the optical image to determine a cropped optical image; a unit for determining an ablation applicator position, configured to obtain an ablation applicator position in the cropped optical image and an ablation applicator position in the ultrasonic image; a unit for determining an overlapping ablation applicator position, configured to make the ablation applicator position in the cropped optical image and the ablation applicator position in the ultrasonic image overlap with each other, to determine an overlapping ablation applicator position; and a unit for determining a thermal ablation region image, configured to perform interpolation processing on the cropped optical image by using the overlapping ablation applicator position as a center, to determine the thermal ablation region image.

In another aspect, the recognition, monitoring, and imaging system specifically includes: a binarization processing module, configured to perform binarization processing on the thermal ablation region image to determine a binary image, where a classification label corresponding to a thermal ablation region in the binary image is 1, and a classification label corresponding to a peripheral area of the thermal ablation region is 0, and the binary image includes a plurality of ultrasonic radiofrequency data points and a classification label corresponding to the ultrasonic radiofrequency data point; a traversing module, configured to traverse the ultrasonic radiofrequency data matrix to divide the ultrasonic radiofrequency data points into a training sample and a test sample; and a module for determining a first classification label, configured to determine, according to the binary image, a training classification label corresponding to the training sample and a test classification label corresponding to the test sample.

In a further aspect, the module for constructing a convolutional neural network specifically includes: a unit for determining a second classification label, configured to obtain an ultrasonic radiofrequency data matrix corresponding to the binary image and the classification label corresponding to the ultrasonic radiofrequency data point; a parameter obtaining unit, configured to determine an ultrasonic scattering echo spectrum estimation parameter and an ultrasonic statistical parameter from scattering echo according to the ultrasonic radiofrequency data matrix, where the ultrasonic scattering echo spectrum estimation parameter include an ultrasonic attenuation parameter, an ultrasonic backscattering parameter, and an ultrasonic scattering sub-characteristic parameter, and the ultrasonic statistical parameter from scattering echo includes an ultrasonic Nakagami parameter, an ultrasonic entropy parameter, and an ultrasonic scattering density parameter; a unit for obtaining a convolutional neural network parameter, configured to obtain a convolutional neural network parameter, where the convolutional neural network parameter includes a convolution kernel size, a number of hidden layers, and a number of feature maps of each layer; and a unit for constructing a convolutional neural network, configured to construct the deep learning model according to the convolutional neural network parameter by sequentially inputting the training sample, the ultrasonic scattering echo spectrum estimation parameter, the ultrasonic statistical parameter from scattering echo, and the classification label corresponding to the ultrasonic radiofrequency data point, where the deep learning model includes the convolutional neural network, the cyclic neural network, and the deep neural network.

The embodiments of the present invention achieve the following technical effects: a recognition, monitoring, and imaging method and system are provided for a thermal ablation region based on ultrasonic deep learning. Based on original ultrasonic radiofrequency data, a to-be-recognized thermal ablation image is determined based on a spatial position correspondence between ultrasonic radiofrequency data points and an optical image by using a convolutional neural network, and a thermal ablation region in an ultrasonic image is recognized based on the to-be-recognized thermal ablation image. In the present invention, the thermal ablation region in the ultrasonic image is recognized based on a machine learning model without relying on several bubbles produced due to high intensity of an ultrasonic echo signal. According to the recognition, monitoring, and imaging method and system provided in the present invention, there is no change when temperature changes, so that recognition accuracy of the thermal ablation region in the ultrasonic image is improved.

BRIEF DESCRIPTION OF THE DRAWINGS

Various additional features and advantages of the invention will become more apparent to those of ordinary skill in the art upon review of the following detailed description of one or more illustrative embodiments taken in conjunction with the accompanying drawings. The accompanying drawings, which are incorporated in and constitute a part of this specification, illustrate one or more embodiments of the invention and, together with the general description given above and the detailed description given below, explain the one or more embodiments of the invention.

DETAILED DESCRIPTION

The following clearly and completely describes the technical solutions in the embodiments of the present invention with reference to the accompanying drawings in the embodiments of the present invention. To make objectives, features, and advantages of the present invention clearer, the following describes embodiments of the present invention in more detail with reference to accompanying drawings and specific implementations.

An objective of the present invention is to provide a recognition, monitoring, and imaging method and system for a thermal ablation region based on ultrasonic deep learning, to improve recognition accuracy of a thermal ablation region in an ultrasonic image. To make the foregoing objective, features, and advantages of the present invention clearer and more comprehensible, the present invention is further described in detail below with reference to the accompanying drawings and specific embodiments.

Figure 1:
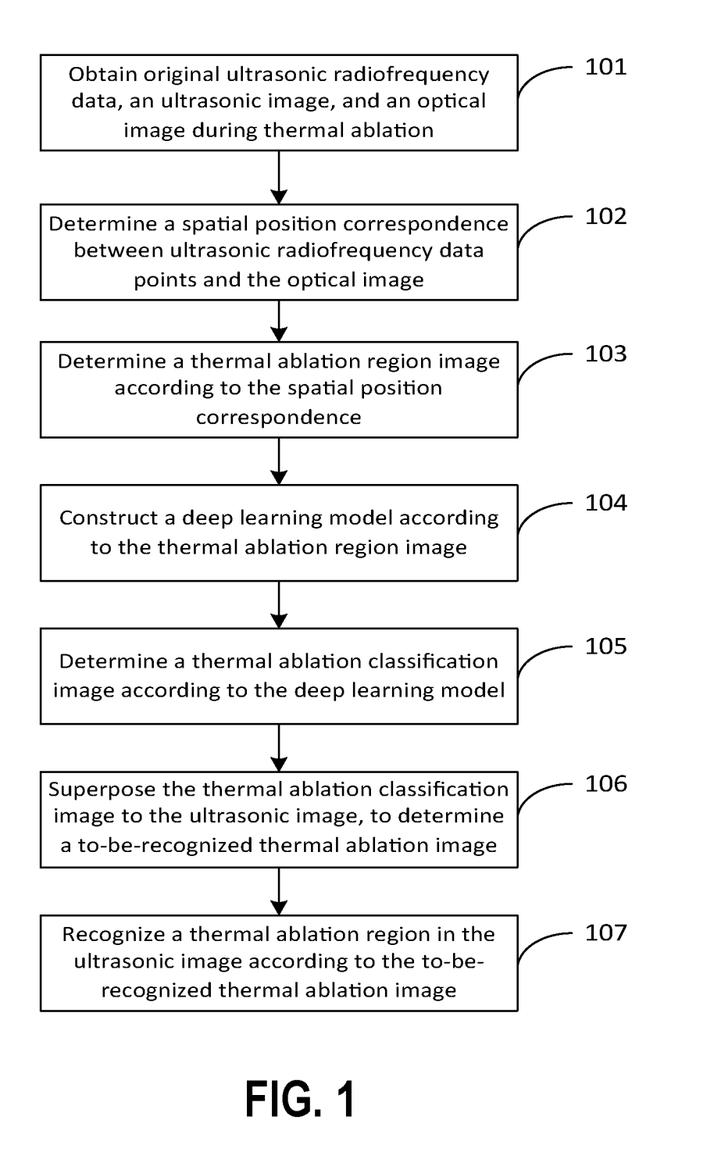
FIG. 1 is a schematic flowchart of a recognition method for a thermal ablation region in an ultrasonic image according to one embodiment of the present invention.

FIG. 1 is a flowchart of a recognition method for a to-be-recognized thermal ablation region in an ultrasonic image according to one embodiment of the present invention. As shown in FIG. 1, the recognition, monitoring, and imaging method for a thermal ablation region based on ultrasonic deep learning includes:

Step 101: Obtain original ultrasonic radiofrequency data, an ultrasonic image, and an optical image during thermal ablation, where the original ultrasonic radiofrequency data includes a plurality of ultrasonic radiofrequency data points; the ultrasonic radiofrequency data point is an ultrasonic scattering echo signal collected by an ultrasonic imaging device; the plurality of ultrasonic radiofrequency data points form an ultrasonic radiofrequency data matrix; and the optical image is captured by a mobile phone or a camera.

Step 102: Make the ultrasonic radiofrequency data points and pixels in the optical image correspond in a one-to-one manner and determine a spatial position correspondence between the ultrasonic radiofrequency data points and the optical image.

Step 103: Determine a thermal ablation region image according to the spatial position correspondence.

Step 103 specifically includes: cropping the optical image to determine a cropped optical image; obtaining an ablation applicator position in the cropped optical image and an ablation applicator position in the ultrasonic image; making the ablation applicator position in the cropped optical image and the ablation applicator position in the ultrasonic image overlap with each other, to determine an overlapping ablation applicator position; and performing interpolation processing on the cropped optical image by using the overlapping ablation applicator position as a center, to determine the thermal ablation region image.

After the performing interpolation processing on the cropped optical image by using the overlapping ablation applicator position as a center, to determine the thermal ablation region image, the method further includes: performing binarization processing on the thermal ablation region image to determine a binary image, where a classification label corresponding to a thermal ablation region in the binary image is 1, and a classification label corresponding to a peripheral area of the thermal ablation region is 0, and the binary image includes a plurality of ultrasonic radiofrequency data points and a classification label corresponding to the ultrasonic radiofrequency data point; traversing the ultrasonic radiofrequency data matrix to divide the ultrasonic radiofrequency data points into a training sample and a test sample; and determining, according to the binary image, a training classification label corresponding to the training sample and a test classification label corresponding to the test sample.

Training samples include a positive sample and a negative sample, where the positive sample indicates an ablation region sample, and the negative sample indicates a normal liver tissue sample. Due to the influence of bubbles and acoustic shielding, an ablation region cannot be accurately obtained from a conventional ultrasonic image. According to the present invention, an ablation region in an ultrasonic data matrix is calibrated by using an ablation region optical image corresponding to the ultrasonic data matrix, and then a training sample is extracted. The extraction process of the training sample is as follows:

(1) Extract an Ablation Region Optical Image

A microwave ablation video image of an in-vitro liver is obtained. The video has recorded a growth situation of an ablation region in the liver in a microwave ablation process. To calibrate an ablation region in an ultrasonic data matrix, an ablation region optical image at a corresponding moment of each frame of ultrasonic data needs to be obtained. A time interval of sample extraction is set to 20 s. An ablation region optical image of the liver at a specific time is extracted from the video according to a sampling time of ultrasonic radiofrequency data, so that there is a corresponding ablation region optical image at the time of each frame of ultrasonic radiofrequency data.

(2) Perform Registration Between an Ultrasonic Data Matrix and the Ablation Region Optical Image An ablation region in ultrasonic radiofrequency data is marked by using the ablation region optical image. Therefore, registration is performed between ultrasonic radiofrequency data and an ablation region optical image of the liver, to implement that sizes of the ultrasonic radiofrequency data and the ablation region optical image of the liver are the same and spatial positions thereof are corresponding to each other.

Figure 2:
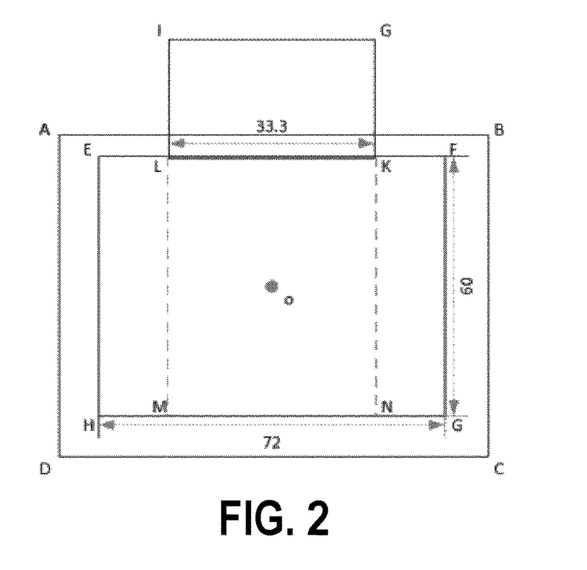
FIG. 2 is a top view showing a registration between an ultrasonic data matrix and an ablation region optical image according to one embodiment of the present invention.
Figure 3A:
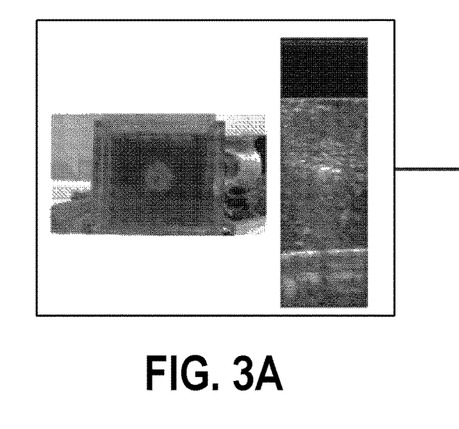
FIG. 3A is a schematic diagram showing an ultrasonic image and an ablation region optical image before registration.
Figure 3B:
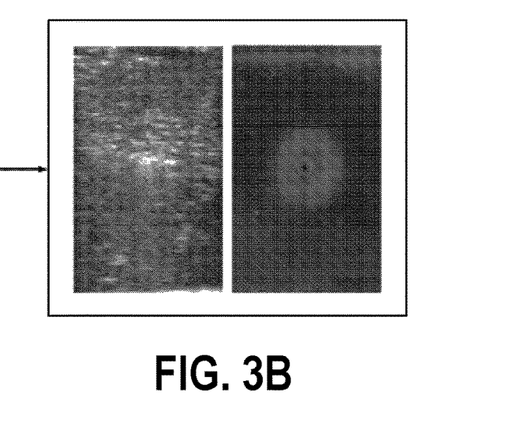
FIG. 3B is a schematic diagram showing the ultrasonic image and the ablation region optical image after registration, following up on FIG. 3A.

A spatial position correspondence between an ultrasonic data collection section and an ablation region optical image is shown in FIG. 2. ABCD indicates the ablation region optical image, EFGH indicates a container containing the liver, IGKL indicates an ultrasonic probe, LKNM indicates the ultrasonic data collection section, and O indicates an ablation applicator position. To implement that sizes of the ultrasonic radiofrequency data and the ablation region optical image of the liver are the same and spatial positions thereof are corresponding to each other, first, the ablation region optical image is cropped to retain only an optical image part of the liver container; then the ablation applicator position is selected in the optical image of the liver container, and coordinates of the position is set to be the same as position coordinates of an ablation applicator position in a microwave ablation ultrasonic image at a corresponding moment; next, with reference to an actual size of the liver container, the optical image of the liver container is cropped to a region with a size of 33.3×53 by using the ablation applicator position as a center; finally, an interpolation operation is performed on the optical image region obtained in the previous step, so that a matrix size in the optical image region and a matrix size of the ultrasonic data collection section at a same time keeps the same. In this case, the sizes of the ultrasonic radiofrequency data and the ablation region optical image of the liver are the same and spatial positions thereof are completely corresponding to each other, and results obtained before and after registration of an ultrasonic image corresponding to the ultrasonic radiofrequency data and the ablation region optical image are shown in FIGS. 3A and 3B.

(3) Calibrate the Ultrasonic Data Matrix

Figure 4A:
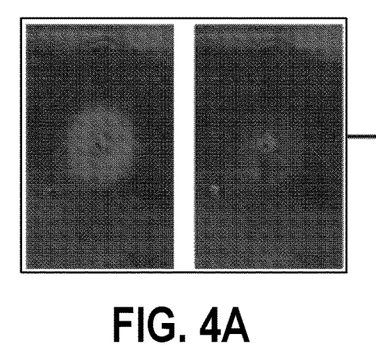
FIG. 4A is a schematic diagram showing sketching and threshold segmentation processing of an optical image according to another embodiment of the present invention.
Figure 4B:
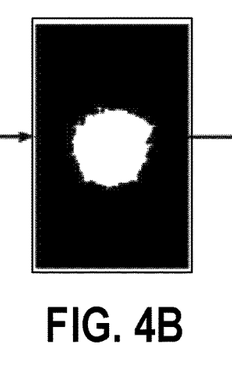
FIG. 4B is a schematic diagram showing binarization processing of the optical image, following up on FIG. 4A.
Figure 4C:
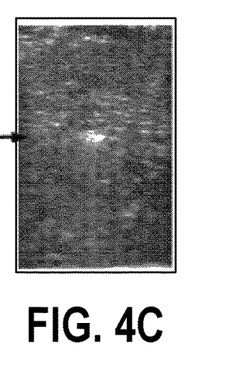
FIG. 4C is a schematic diagram showing calibration of the ultrasonic data matrix following up on FIG. 4A.

Image sketching and threshold segmentation are performed on the ablation region optical image, an ablation region optical image at a moment 0 is subtracted from the ablation region optical image at a current moment, and noise in the image is filtered by using a threshold, to obtain an edge of an ablation region at the current moment. On this basis, an ablation region in the ultrasonic image at an ablation end moment is calibrated. A tissue within a boundary is in an ablation region that belongs to a thermal ablation category, while a region outside the boundary belongs to a non-thermal ablation category. Therefore, a label category corresponding to each point in the ultrasonic data matrix is obtained. An ultrasonic data calibration process is shown in FIGS. 4A-4C.

The accuracy of a classification label of a training sample is of great significance to improve the classification performance of a convolutional neural network. To verify the accuracy of the ablation region obtained by using the above experimental method, pathological analysis is performed on an ablated pig liver tissue, and HE staining results at different magnifications are shown in FIGS. 5A-5C.

Figure 5A:
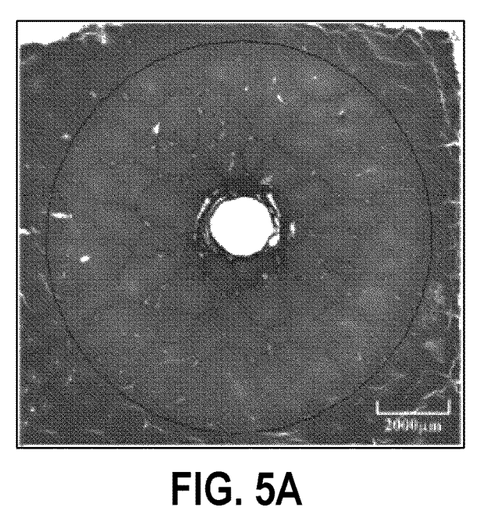
FIG. 5A is a HE staining diagram showing calibration of a pork liver tissue in a thermal ablation region according to another embodiment of the present invention.
Figure 5B:
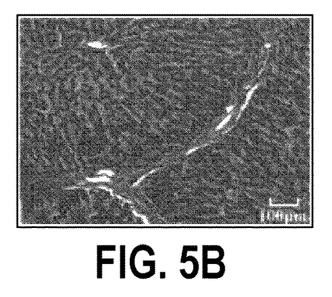
FIG. 5B is a HE staining diagram showing a thermal ablation region of the pork liver tissue of FIG. 5A.
Figure 5C:
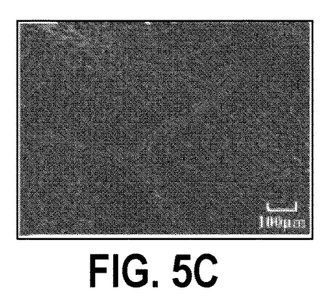
FIG. 5C is a HE staining diagram showing a non-ablation thermal area of the pork liver tissue of FIG. 5A.

To this end, FIG. 5A shows the pig liver tissue in a calibrated ablation region; FIG. 5B shows an ablation region of the pig liver tissue; and FIG. 5C shows a non-ablation region of the pig liver tissue. According to the results shown, it can be learned that a structure of a normal liver tissue is relatively complete, and cells of the normal liver tissue are tightly bound together. After microwave ablation, a liver plate in the liver tissue is ruptured and an intercellular space is increased. In this specification, ablation regions in HE staining images of four groups of pig livers are calibrated, areas of the ablation regions are calculated based on calibration results of the ablation regions; areas of the ablation regions are calculated by using the data calibration method shown in FIGS. 4A-4C; and area accuracy is calculated by dividing the former obtained area from the later obtained area, and its value is 1.19±0.07. That is, an area of an ablation region obtained by sketching an ablation region optical image is larger than an area of an ablation region obtained through image HE staining. However, considering that a production process of HE stained tissue sections leads to tissue atrophy, the ablation region obtained through image HE staining actually is less than an actual ablation region. In addition, in a microwave ablation process of a clinical tumor, it is required that the actual ablation region should be larger than the area in which the tumor is located. Therefore, the ultrasonic data calibration method shown in FIGS.

4A-4C is feasible and can obtain relatively accurate a classification label of a training sample.

(4) Extract a Training Sample

The classification label corresponding to each point in the ultrasonic data matrix has been obtained, but each point herein can only provide its amplitude information, and don't have much significance for the actual classification. Therefore, a matrix with a current classification point as a center is selected as the training sample. Selecting the matrix as the training sample has such two advantages.

First, the matrix includes a relationship between the current classification point and an amplitude of a surrounding environment.

Second, the matrix can express a texture feature near the point, which is of great value for correct classification. A new problem is also introduced when the matrix is used to replace a point for classified training. When a large matrix is used as a training sample, although the accuracy of classification can be improved, but the amount of data computing is greatly improved. For real-time monitoring of thermal ablation, it is necessary to reduce the amount of data computing. Therefore, while improving the recognition accuracy of an ablation region, to ensure the real-time performance of an ultrasonic monitoring effect, selection of a training sample size is very important. To further reduce the amount of data computing, a training sample is extracted from the ultrasonic radio-frequency data matrix in an interval sampling manner.

Step 104: Construct a deep learning model according to the thermal ablation region image, where the deep learning model includes a convolutional neural network, a cyclic neural network, and a deep neural network.

The constructing a deep learning model according to the thermal ablation region image, where the deep learning model includes a convolutional neural network, a cyclic neural network, and a deep neural network specifically includes: obtaining an ultrasonic radiofrequency data matrix corresponding to the binary image and the classification label corresponding to the ultrasonic radiofrequency data point; determining an ultrasonic scattering echo spectrum estimation parameter and an ultrasonic statistical parameter from scattering echo according to the ultrasonic radiofrequency data matrix, where the ultrasonic scattering echo spectrum estimation parameter includes an ultrasonic attenuation parameter, an ultrasonic backscattering parameter, and an ultrasonic scattering sub-characteristic parameter, and the ultrasonic statistical parameter from scattering echo includes an ultrasonic Nakagami parameter, an ultrasonic entropy parameter, and an ultrasonic scattering density parameter; obtaining a convolutional neural network parameter, where the convolutional neural network parameter includes a convolution kernel size, a number of hidden layers, and a number of feature maps of each layer; and constructing the deep learning model according to the convolutional neural network parameter by sequentially inputting the training sample, the ultrasonic scattering echo spectrum estimation parameter, the ultrasonic statistical parameter from scattering echo, and the classification label corresponding to the ultrasonic radiofrequency data point, where the deep learning model includes the convolutional neural network, the cyclic neural network, and the deep neural network.

Step 105: Determine a thermal ablation classification image according to the deep learning model.

In addition, another deep learning method may be used to recognize a thermal ablation region in the ultrasonic image, for example, by using the cyclic neural network or a recurrent neural network.

Step 106: Superpose the thermal ablation classification image to the ultrasonic image, to determine a to-be-recognized thermal ablation image.

Step 107: Recognize a thermal ablation region in the ultrasonic image according to the to-be-recognized thermal ablation image.

Based on the recognition, monitoring, and imaging method provided in the present invention, the present invention proposes a thermal ablation ultrasonic monitoring and imaging method based on ultrasonic deep learning, specifically including the following steps:

Step 1: Collect ultrasonic radiofrequency data of a heat coagulation part in a microwave thermal ablation process of an in-vitro pork liver microwave, where an ablation time is 5 min, and sampling frequency is set to 0.2 times/s; and use a mobile phone to capture a video to record a changing status of a thermal ablation region, where a camera position and an ultrasonic radiofrequency data collection position are on a same cross section; extract a specific frame rate in the thermal ablation video, so that ultrasonic radiofrequency data at each moment is corresponding to a thermal ablation photo, where in addition to using a microwave manner for thermal ablation, a thermal ablation technology further includes an ablation manner such as radiofrequency ablation and laser ablation.

Step 2: Find points corresponding to three spatial positions of a thermal ablation photo and ultrasonic radiofrequency data, crop the thermal ablation photo, and perform a related translation operation and an interpolation operation to make a pixel in the thermal ablation photo correspond to an ultrasonic radiofrequency data point in a one-to-one manner.

Step 3: Draw a heat coagulation area in the thermal ablation photo by using a threshold segmentation method, where a position corresponding to a value greater than a threshold is considered as a thermal ablation region, and another area is a normal area; convert the photo into a binary image; set an amplitude of the heat coagulation area to 1 and set an amplitude of a peripheral area to 0, to be used as classification labels.

Step 4: Obtain an ultrasonic attenuation parameter matrix and an ultrasonic Nakagami parameter matrix according to a physical property of ultrasound through calculation by using an ultrasonic radiofrequency data matrix.

Figure 6:
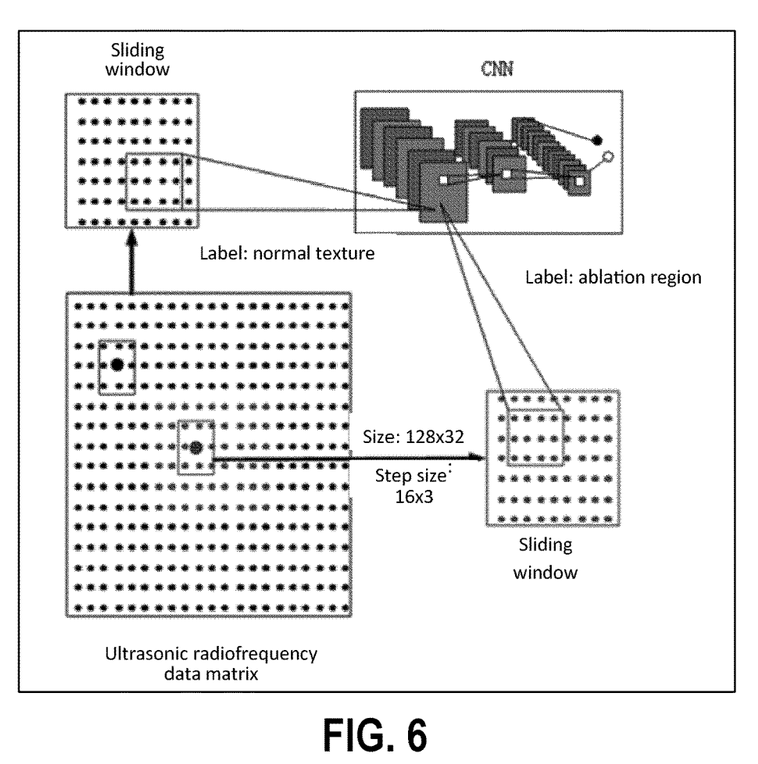
FIG. 6 is a diagram illustrating extraction of a training sample according to an embodiment of the present invention.

Step 5: As shown in FIG. 6, to reduce operation complexity, traverse the ultrasonic radiofrequency data matrix at a step size of 16*3, extract a matrix with a size of 128*28 (actual corresponding size is 4 mm*4 mm) by using a traversing point as a center, where the matrix is a training sample, and a value of a position corresponding to this point in the thermal ablation binary photo is a classification label.

Step 6: Construct a deep learning model, where the deep learning model includes a convolutional neural network, a cyclic neural network, and a deep neural network; set a convolutional kernel size, a quantity of hidden layer, and several feature maps of each layer. First, the training sample is input; an attenuation parameter feature and an ultrasonic Nakagami parameter feature are sequentially input after a neural network extracts an advanced feature capable of representing thermal damage is extracted by using a neural network, to complete training of the neural network, and obtain a model parameter of the neural network.

Step 7: Divide a to-be-measured ultrasonic radiofrequency matrix into several matrixes with small sizes according to content described in step 4, obtain an attenuation parameter matrix and a Nakagami parameter matrix through calculation, and successively input these values into the trained convolutional neural network, to obtain an initial classification result.

Figure 7:
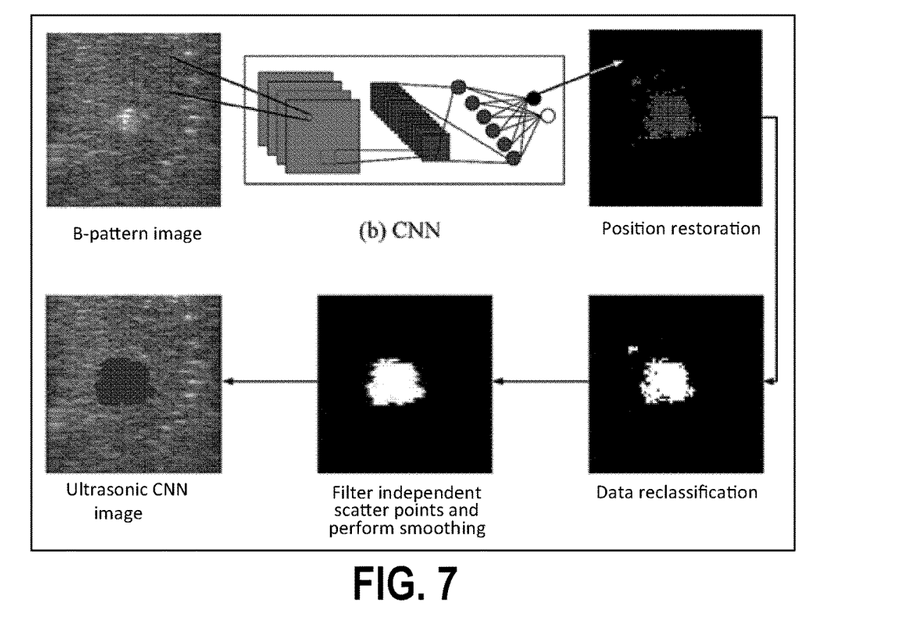
FIG. 7 is a flowchart showing a series of steps in thermal ablation imaging based on a convolutional neural network according to one embodiment.

Step 8: As shown in FIG. 7, obtain a binary matrix of the classification result according to a spatial position correspondence, draw a binary image of the binary matrix, remove independent scatter points in the image, and smooth an edge of the thermal ablation region, to obtain a thermal ablation classification image.

Figure 8:
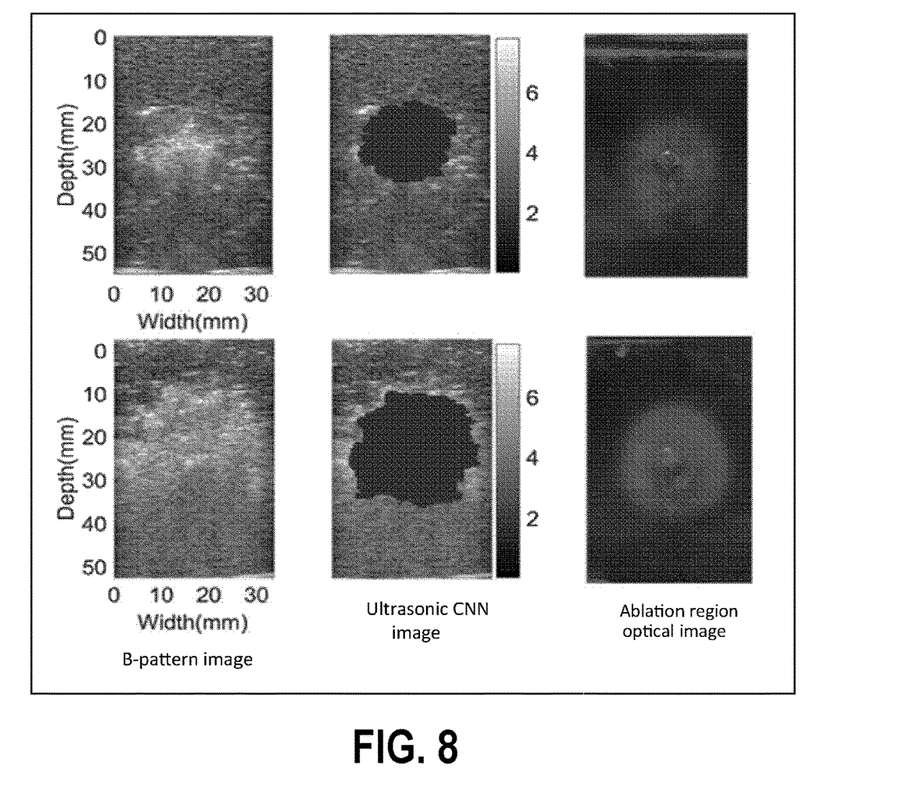
FIG. 8 is a series of diagrams showing a B-pattern image, an ultrasonic CNN image, and an ablation region image according to one embodiment.

Step 9: As shown in FIG. 8, superpose the obtained thermal ablation classification image to an ultrasonic image, label the thermal ablation region, and retain an ultrasonic image result of a surrounding normal tissue.

By using the recognition method provided in the present invention, the following effects can be achieved.

First, because feature information included in the ultrasonic image is very limited, while the original ultrasonic radiofrequency data includes acoustic parameter information such as reflection, scattering, and attenuation information, to ensure that enough classification features can be extracted by using the convolutional neural network, in the present invention, the original ultrasonic radiofrequency data is used as a training sample, to improve accuracy of thermal ablation recognition.

Second, it is difficult to obtain an accurate thermal ablation region from a conventional ultrasonic image. To obtain a more accurate classification label, position matching is performed on the thermal ablation photo and the ultrasonic radiofrequency data, and a thermal ablation position in the photo is used as a gold standard of a classification label, to improve accuracy of thermal ablation.

Third, an attenuation coefficient and a Nakagami parameter are important parameters expressing a tissue characteristic. Ultrasonic parameters such as the attenuation coefficient and the Nakagami parameter are obtained through manual feature extraction, these manually extracted features and features automatically extracted by using the convolutional neural network are jointly used for thermal ablation region recognition, to improve classification accuracy.

Figure 9:
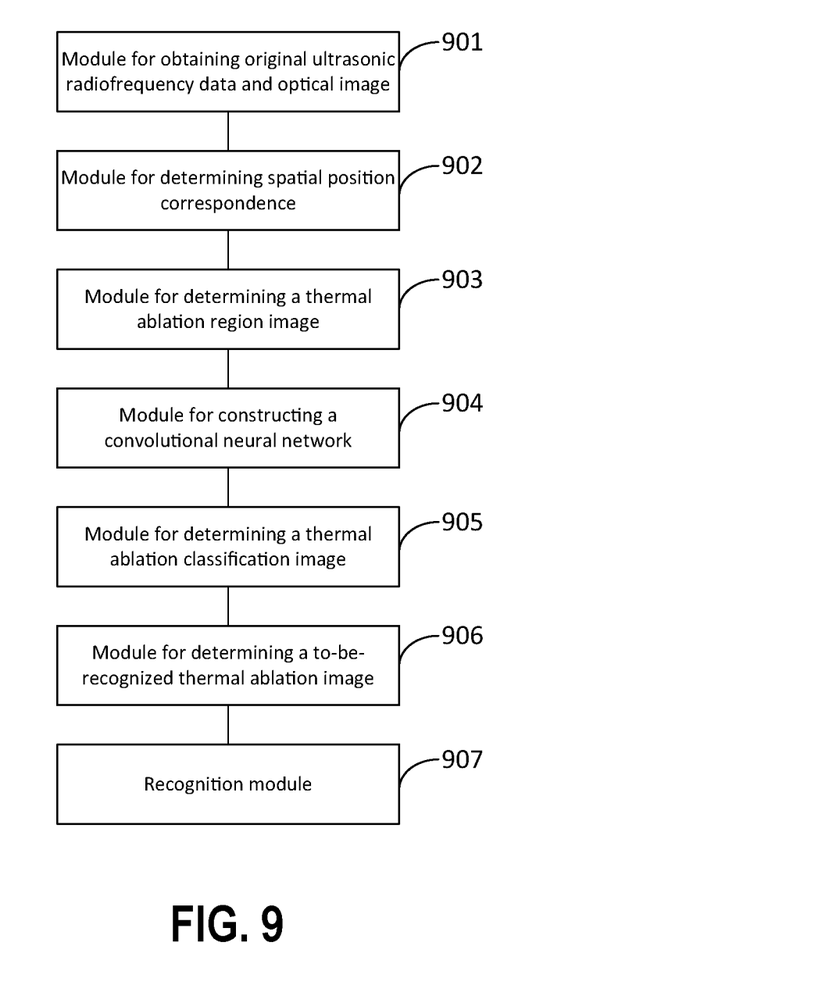
FIG. 9 is a schematic structural diagram of a recognition system for a thermal ablation region in an ultrasonic image according to a further embodiment of the present invention.

FIG. 9 is a structural diagram of a recognition system for a to-be-recognized thermal ablation region in an ultrasonic image according to one embodiment of the present invention. As shown in FIG. 9, the recognition system for a thermal ablation region based on ultrasonic deep learning includes a module for obtaining original ultrasonic radiofrequency data and optical image 901, a module for determining spatial position correspondence 902, a module for determining a thermal ablation region image 903, a module for constructing a convolutional neural network 904, a module for determining a thermal ablation classification image 905, a module for determining a to-be-recognized thermal ablation image 906, and the recognition module 907.

The module for obtaining original ultrasonic radiofrequency data and optical image 901 is configured to obtain original ultrasonic radiofrequency data, an ultrasonic image, and an optical image during thermal ablation, where the original ultrasonic radiofrequency data includes a plurality of ultrasonic radiofrequency data points; the ultrasonic radiofrequency data point is an ultrasonic scattering echo signal collected by an ultrasonic imaging device; the plurality of ultrasonic radiofrequency data points form an ultrasonic radiofrequency data matrix; and the optical image is captured by a mobile phone or a camera.

The module for determining spatial position correspondence 902 is configured to make the ultrasonic radiofrequency data points and pixels in the optical image correspond in a one-to-one manner and determine a spatial position correspondence between the ultrasonic radiofrequency data points and the optical image.

The module for determining a thermal ablation region image 903, configured to determine a thermal ablation region image according to the spatial position correspondence.

The module for determining a thermal ablation region image 903 specifically includes: a cropping unit, configured to crop the optical image to determine a cropped optical image; a unit for determining an ablation applicator position, configured to obtain an ablation applicator position in the cropped optical image and an ablation applicator position in the ultrasonic image; a unit for determining an overlapping ablation applicator position, configured to make the ablation applicator position in the cropped optical image and the ablation applicator position in the ultrasonic image overlap with each other, to determine an overlapping ablation applicator position; and a unit for determining a thermal ablation region image, configured to perform interpolation processing on the cropped optical image by using the overlapping ablation applicator position as a center, to determine the thermal ablation region image.

The module for constructing a convolutional neural network 904 is configured to construct a deep learning model according to the thermal ablation region image, where the deep learning model includes a convolutional neural network, a cyclic neural network, and a deep neural network.

The module for constructing a convolutional neural network 904 specifically includes: a unit for determining a second classification label, configured to obtain an ultrasonic radiofrequency data matrix corresponding to a binary image and the classification label corresponding to the ultrasonic radiofrequency data point; a parameter obtaining unit, configured to determine an ultrasonic scattering echo spectrum estimation parameter and an ultrasonic statistical parameter from scattering echo according to the ultrasonic radiofrequency data matrix, where the ultrasonic scattering echo spectrum estimation parameter includes an ultrasonic attenuation parameter, an ultrasonic backscattering parameter, and an ultrasonic scattering sub-characteristic parameter, and the ultrasonic statistical parameter from scattering echo includes an ultrasonic Nakagami parameter, an ultrasonic entropy parameter, and an ultrasonic scattering density parameter; a unit for obtaining a convolutional neural network parameter, configured to obtain a convolutional neural network parameter, where the convolutional neural network parameter includes a convolution kernel size, a number of hidden layers, and a number of feature maps of each layer; and a unit for constructing a convolutional neural network, configured to construct the deep learning model according to the convolutional neural network parameter by sequentially inputting the training sample, the ultrasonic scattering echo spectrum estimation parameter, the ultrasonic statistical parameter from scattering echo, and the classification label corresponding to the ultrasonic radiofrequency data point, where the deep learning model includes the convolutional neural network, the cyclic neural network, and the deep neural network.

The module for determining a thermal ablation classification image 905 is configured to determine a thermal ablation classification image according to the deep learning model.

The module for determining a to-be-recognized thermal ablation image 906 is configured to superpose the thermal ablation classification image to the ultrasonic image, to determine a to-be-recognized thermal ablation image.

The recognition module 907 is configured to recognize a thermal ablation region in the ultrasonic image according to the to-be-recognized thermal ablation image.

The recognition system provided in the present invention further includes: a binarization processing module, configured to perform binarization processing on the thermal ablation region image to determine a binary image, where a classification label corresponding to a thermal ablation region in the binary image is 1, and a classification label corresponding to a peripheral area of the thermal ablation region is 0, and the binary image includes a plurality of ultrasonic radiofrequency data points and a classification label corresponding to the ultrasonic radiofrequency data point; a traversing module, configured to traverse the ultrasonic radiofrequency data matrix to divide the ultrasonic radiofrequency data points into a training sample and a test sample; and a module for determining a first classification label, configured to determine, according to the binary image, a training classification label corresponding to the training sample and a test classification label corresponding to the test sample.

The present invention relates to an ultrasonic monitoring and imaging method for a thermal ablation process based on deep learning. In the method, a thermal damage image captured during thermal ablation is used as a classification label in a convolutional neural network. Considering advantages of automatic feature extraction and manual feature extraction in deep learning, when ultrasonic radiofrequency data is used as an input sample, advanced features obtained through manual extraction, such as an ultrasonic attenuation coefficient of a tissue and a Nakagami parameter of the tissue, are also input. The three are jointly used in training of the convolutional neural network, to improve the accuracy of recognizing a thermal ablation region by using the convolutional neural network.

Several examples are used for illustration of the principles and implementation methods of the present invention. The description of the embodiments is used to help illustrate the method and its core principles of the present invention. In addition, those skilled in the art can make various modifications in terms of specific embodiments and scope of application in accordance with the teachings of the present invention. In conclusion, the content of this specification shall not be construed as a limitation to the invention.

The embodiments described above are only descriptions of preferred embodiments of the present invention and are not intended to limit the scope of the present invention. Various variations and modifications can be made to the technical solution of the present invention by those of ordinary skill in the art, without departing from the design and spirit of the present invention. The variations and modifications should all fall within the claimed scope defined by the claims of the present invention.

What is claimed is:

1. A recognition, monitoring, and imaging system for a thermal ablation region based on ultrasonic deep learning, comprising:
    a module for obtaining original ultrasonic radiofrequency data and an optical image, configured to obtain original ultrasonic radiofrequency data, an ultrasonic image, and the optical image during thermal ablation, wherein the original ultrasonic radiofrequency data comprises a plurality of ultrasonic radiofrequency data points; the ultrasonic radiofrequency data point is an ultrasonic scattering echo signal collected by an ultrasonic imaging device; the plurality of ultrasonic radiofrequency data points form an ultrasonic radiofrequency data matrix; and the optical image is captured by a mobile phone or a camera such that the optical image has a plurality of pixels;
    a module for determining a spatial position correspondence, configured to make the ultrasonic radiofrequency data points and the pixels in the optical image correspond in a one-to-one manner, and determine the spatial position correspondence between the ultrasonic radiofrequency data points and the optical image;
    a module for determining a thermal ablation region image, configured to determine the thermal ablation region image according to the spatial position correspondence;
    a module for constructing a convolutional neural network, configured to construct a deep learning model according to the thermal ablation region image, wherein the deep learning model comprises a convolutional neural network, a cyclic neural network, and a deep neural network;
    a module for determining a thermal ablation classification image, configured to determine the thermal ablation classification image according to the deep learning model;
    a module for determining a thermal ablation recognition image, configured to superpose the thermal ablation classification image to the ultrasonic image, to determine the thermal ablation recognition image; and
    a recognition module, configured to recognize a thermal ablation region in the ultrasonic image according to the thermal ablation recognition image.

2. The recognition, monitoring, and imaging system of claim 1, wherein the module for determining the thermal ablation region image further comprises:
    a cropping unit configured to crop the optical image to determine a cropped optical image;
    a unit for determining an ablation applicator position, configured to obtain a first ablation applicator position in the cropped optical image and a second ablation applicator position in the ultrasonic image;
    a unit for determining an overlapping ablation applicator position, configured to make the first ablation applicator position in the cropped optical image and the second ablation applicator position in the ultrasonic image overlap with each other, to determine the overlapping ablation applicator position; and
    a unit for obtaining the thermal ablation region image, configured to perform interpolation processing on the cropped optical image by using the overlapping ablation applicator position as a center, to determine the thermal ablation region image.

3. The recognition, monitoring, and imaging system of claim 2, further comprising:
    a binarization processing module, configured to perform binarization processing on the thermal ablation region image to determine a binary image, wherein a classification label corresponding to a thermal ablation region in the binary image is 1, and a classification label corresponding to a peripheral region of the thermal ablation region is 0, and the binary image comprises a plurality of ultrasonic radiofrequency data points and a classification label corresponding to the ultrasonic radiofrequency data point;

a traversing module configured to traverse the ultrasonic radiofrequency data matrix to divide the ultrasonic radiofrequency data points into a training sample and a test sample; and a module for determining a first classification label, configured to determine, according to the binary image, a training classification label corresponding to the training sample and a test classification label corresponding to the test sample.

4. The recognition, monitoring, and imaging system of claim 3, wherein the module for constructing the convolutional neural network further comprises:

a unit for determining a second classification label, configured to obtain an ultrasonic radiofrequency data matrix corresponding to the binary image and the classification label corresponding to the ultrasonic radiofrequency data point;

a parameter obtaining unit, configured to determine an ultrasonic scattering echo spectrum estimation parameter and an ultrasonic statistical parameter from scattering echo according to the ultrasonic radiofrequency data matrix, wherein the ultrasonic scattering echo spectrum estimation parameter comprises an ultrasonic attenuation parameter, an ultrasonic backscattering parameter, and an ultrasonic scattering sub-characteristic parameter, and the ultrasonic statistical parameter from scattering echo comprises an ultrasonic Nakagami parameter, an ultrasonic entropy parameter, and an ultrasonic scattering density parameter;

a unit for obtaining a convolutional neural network parameter, configured to obtain the convolutional neural network parameter, wherein the convolutional neural network parameter comprises a convolution kernel size, several hidden layers, and several feature maps of each layer; and a unit for building the convolutional neural network, configured to construct the deep learning model according to the convolutional neural network parameter by sequentially inputting the training sample, the ultrasonic scattering echo spectrum estimation parameter, the ultrasonic statistical parameter from scattering echo, and the classification label corresponding to the ultrasonic radiofrequency data point.

* * * * *